US010074764B2

United States Patent
Stevenson et al.

(10) Patent No.: US 10,074,764 B2
(45) Date of Patent: Sep. 11, 2018

(54) METHOD OF FABRICATING X-RAY ABSORBERS FOR LOW-ENERGY X-RAY SPECTROSCOPY

(71) Applicant: The United States of America as represented by the Administrator of the National Aeronautics and Space Administration, Washington, DC (US)

(72) Inventors: Thomas R. Stevenson, Rockville, MD (US); Manuel A. Balvin, Springfield, VA (US); Kevin L. Denis, Crofton, MD (US); John E. Sadleir, Washington, DC (US); Peter C. Nagler, College Park, MD (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 15/280,369

(22) Filed: Sep. 29, 2016

(65) Prior Publication Data

US 2018/0090662 A1    Mar. 29, 2018

(51) Int. Cl.
| | | |
|---|---|---|
| H01L 31/115 | (2006.01) | |
| H01L 31/18 | (2006.01) | |
| G01N 23/083 | (2018.01) | |
| G01T 1/12 | (2006.01) | |
| G01T 1/36 | (2006.01) | |
| H01L 39/24 | (2006.01) | |
| H01L 21/027 | (2006.01) | |

(Continued)

(52) U.S. Cl.
CPC .......... *H01L 31/18* (2013.01); *G01N 23/083* (2013.01); *G01T 1/006* (2013.01); *G01T 1/36* (2013.01); *G21K 1/10* (2013.01); *H01L 21/027* (2013.01); *H01L 31/085* (2013.01); *H01L 39/24* (2013.01)

(58) Field of Classification Search
CPC ..... H01L 31/085; H01L 31/18; G01N 23/063; G01N 23/083
USPC .......... 257/428, E31.086, E31.087, E31.092; 438/57; 378/51, 53
See application file for complete search history.

(56) References Cited

U.S. PATENT DOCUMENTS

| | | | | |
|---|---|---|---|---|
| 4,328,298 A | * | 5/1982 | Nester ....................... | G03F 1/22 216/100 |
| 5,266,183 A | * | 11/1993 | Dauksher ................. | C25D 3/48 205/266 |
| 2015/0085974 A1 | * | 3/2015 | Shew ........................ | G03F 1/22 378/35 |

OTHER PUBLICATIONS

Nagler et al., Fabrication of Magnetic Penetration Thermometers (MPTs) Optimized for Soft X-ray Spectroscopy (Abstract Only), International Workshop on Low Temperature Detectors (LTD-15), Pasadena California, Jun. 24-28, 2013.*

(Continued)

*Primary Examiner* — Julio J Maldonado
*Assistant Examiner* — Molly Reida
(74) *Attorney, Agent, or Firm* — Christopher O. Edwards; Bryan A. Geurts; Mark P. Dvorscak

(57) ABSTRACT

A method of forming low-energy x-ray absorbers. Sensors may be formed on a semiconductor, e.g., silicon, wafer. A seed metal layer, e.g., gold, is deposited on the wafer and patterned into stem pads for electroplating. Stems, e.g., gold, are electroplated from the stem seed pads through a stem mask. An absorber layer, e.g., gold, is deposited on the wafer, preferably e-beam evaporated. After patterning the absorbers, absorber and stem mask material is removed, e.g., in a solvent bath and critical point drying.

22 Claims, 5 Drawing Sheets

(51) Int. Cl.
G21K 1/10 (2006.01)
H01L 31/08 (2006.01)
G01T 1/00 (2006.01)

(56) References Cited

OTHER PUBLICATIONS

Brown et al., Absorber Materials for Transition-Edge Sensor X-ray Microcalorimeters, 2007.*
Nagler et al., Fabrication of Magnetic Penetration Thermometers (MPTs) Optimized for Soft X-ray Spectrscopy (Poster), International Workshop on Low Temperature Detectors (LTD-15), Pasadena California, Jun. 24-28, 2013.*
Tralshawala et al., Design and fabrication of superconducting transition edge X-ray calorimeters, Nuclear Instruments and Methods in Physics Research A 444 (2000) 188-191.*
Nagler et al., Performance of Magnetic Penetration Thermometers for X-ray Astronomy, J Low Temp Phys (2012) 167:455-460.*
Bailey, CN.; Adams, J. S.; Bandler, S. R.; Brekosky, R. P.; Chervenak, J. A.; Eckart, M. E.; Finkbeiner, F. M.; Kelley, R. L.; Kelly, D. P.; Kilbourne, C. A.; Porter, F. S.; Sadleir, J. E.; Smith, SJ. Implications of Weak Link Effects on Thermal Characteristics of Transition-Edge Sensors. Journal of Low Temperature Physics, vol. 167, issue 3-4, pp. 121-128 (2012).
N. Iyomoto • S.R. Bandler • R.P. Brekosky • A.-D. Brown • J.A. Chervenak • E. Figueroa-Feliciano • F.M. Finkbeiner • R. L. Kelley • C.A. Kilbourne • M.A. Lindeman • F.S. Porter • T. Saab • J.E. Sadleir • S.J. Smith. Modeling of TES X-Ray Microcalorimeters with a Novel Absorber Design. J Low Temp Phys 151: 406-412 (2008).
M. E. Eckart, J. S. Adams, S. R. Bandler, R. P. Brekosky, A.-D. Brown, J. A. Chervenak, A. J. Ewin, F. M. Finkbeiner, R. L. Kelley, C. A. Kilbourne, F. S. Porter, J. E. Sadleir, S. J. Smith, E. Figueroa-Feliciano, and P. Wikus Large-Absorber TES X-ray Microcalorimeters and the Micro-X Detector Array. AIP Conference Proceedings 1185, 699 (2009).
Wen-Ting Hsieh, Simon R. Bandler, Daniel P. Kelly, Jan P. Porst, Hannes Rotzinger, George M. Seidel, and Thomas R. Stevenson. Microfabrication of High Resolution X-ray Magnetic Calorimeters. AIP Conference Proceedings 1185, 591 (2009).
J.-P. Porst, S. R. Bandler • J. S. Adams • M. A. Balvin • S. E. Busch • M. E. Eckart • R. L. Kelley • C. A. Kilbourne • S. J. Lee • P. C. Nagler • F. S. Porter • J. E. Sadleir • G. M. Characterization and Performance of Magnetic Calorimeters for Applications in X-ray Spectroscopy. J Low Temp Phys 176:617-623 (2014).

P.C. Nagler, J.S. Adams, M.A. Balvin • S.R. Bandler • K.L. Denis • W.-T. Hsieh • D.P. Kelly • J.-P. Porst • J.E. Sadleir • G.M. Seidel • S.J. Smith • T.R. Stevenson. Performance of Magnetic Penetration Thermometers for X-ray Astronomy. J Low Temp Phys 167:455-460 (2012).
Suan Hui Pu, Andrew S. Holmes, Eric M. Yeatman. Stress in electroplated gold on silicon substrates and its dependence on cathode agitation. Microelectronic Engineering 112 21-26 (2013).
H. Rotzinger • J. Adams • S.R. Bandler • J. Beyer • H. Eguchi • E. Figueroa-Feliciano • W. Hsieh • G.M. Seidel • T. Stevenson. Performance of Micro-fabricated Magnetic Calorimeters Arrays for X-Ray Spectroscopy. J Low Temp Phys 151: 351-356 (2008).
Simon R. Bandler, Joseph S. Adams, Joern Beyer, Wen-Ting Hsieh, Richard L. Kelley, Caroline A. Kilbourne, Jan-Patrick Porst, F. Scott Porter, Hannes Rotzinger, George M. Seidel, Stephen J. Smith, and Thomas R.Stevenson. Performance of High-Resolution, Microfabricated, X-ray Magnetic Calorimeters. AIP Conference Proceedings 1185, 579 (2009).
S.R. Bandler, R.P. Brekosky, A.-D. Brown, J.A. Chervenak, E. Figueroa-Feliciano, F.M. Finkbeiner, N. Iyomoto, R.L. Kelley, C.A. Kilbourne • F.S. Porter, J. Sadleir, S.J. Smith. Performance of TES X-ray Microcalorimeters with a Novel Absorber Design. J Low Temp Phys 151: 400-405(2008).
T. R. Stevenson, M. A. Balvin, S. R. Bandler, S. E. Busch, K. L. Denis, W.-T. Hsieh, D. P. Kelly, W. Merrell, P. C. Nagler, J.-P. Porst, J. E. Sadleir, G. M. Seidel, and S. J. Smith. Superconducting Effects in Optimization of Magnetic Penetration Thermometers for X-Ray Microcalorimeters. IEEE Transactions of Applied Superconductivity, vol. 23, No. 3, (2013).
S.J. Smith, S.R. Bandler, R.P. Brekosky, A.-D. Brown, J.A. Chervenak, M.E. Eckart, F.M. Finkbeiner, R.L. Kelley, C.A. Kilbourne, F.S. Porter, E. Figueroa-Feliciano, Development of arrays of position-sensitive microcalorimeters for Constellation-X, in Space Telescopes and Instrumentation 2008: Ultraviolet to Gamma Ray, edited by M. J. L. Turner and K. A. Flanagan, proceedings of the Society of Photo-Optical Instrumentation Engineers (SPIE), vol. 7011, article 701126 (2008).
S.J. Smith, S.R. Bandler, R.P. Brekosky, A.-D. Brown, J.A. Chervenak, M.E. Eckart, E. Figueroa-Feliciano, F.M. Finkbeiner, N. Iyomoto, R.L. Kelley, C.A. Kilbourne, F.S. Porter, J.E. Sadleir, Development of position-sensitive transition-edge sensor X-ray detectors, IEEE Transactions on Applied Superconductivity, 19(3) 451-455 (2009).
S.J. Smith, S.R. Bandler, J. Beyer, J.A. Chervenak, D. Drung, M.E. Eckart, F.M. Finkbeiner, R.L. Kelley, C.A. Kilbourne, F.S. Porter, J.E. Sadleir, Extended focal plane array development for the International X-ray Observatory, AIP conference Proc. 1185 707-710 (2009).

* cited by examiner

METHOD OF FABRICATING X-RAY ABSORBERS FOR LOW-ENERGY X-RAY SPECTROSCOPY

ORIGIN OF THE INVENTION

The invention described herein was made by an employee of the United States Government, and may be manufactured and used by or for the Government for governmental purposes without the payment of any royalties thereon or therefor.

BACKGROUND OF THE INVENTION

Field of the Invention

The present invention is generally related to x-ray spectroscopy and more particularly to fabricating x-ray absorbers for sensing low energy x-rays, especially in high-resolution x-ray microcalorimeters used in spaceborne x-ray spectroscopy applications.

Background Description

For future rocket-based spectroscopy missions National Aeronautics and Space Administration (NASA) requires high-resolution x-ray microcalorimeters with large pixel viewing areas, capable of low-energy measurements below one thousand electron volts (<1 keV). State of the art microfabrication techniques have been used successfully to fabricate higher energy suspended x-ray absorbers, optimized for 1-10 keV. While, higher energy absorbers can be fairly thick titanium/gold or titanium/gold/bismuth, these thick absorbers are unusable below 1 keV. While, higher energy absorbers can be fairly thick metal bilayers or tri-layers, e.g. titanium/gold or titanium/gold/bismuth, these thick absorbers are unusable below 1 keV. Sensing low energy requires an absorber with a significantly thinner, larger area pixel that has very few small thermal contact stems (focus-points for collected energy). The stems are thermally coupled to, or couple-able to, a temperature sensor for sensing collected energy and a substrate as a thermal mass for recovering or resetting from incident energy.

Unfortunately, the microfabrication techniques traditionally used for thick absorbers (>1 μm thick) in state-of-the-art high-energy x-ray microcalorimeters are unusable for manufacturing thinner (0.3 micrometers or microns) absorbers that are necessary for low-energy applications. Traditionally, absorbers have been formed by masking a wafer for stems, reflowing the mask photoresist to soften/round mask edges, sputter the gold stems and electroplate absorbers to an adhesion, or seed, layer on the mask and stems. This created steep angles at the absorbers adjacent to stems, which isn't a problem if the absorber is thick enough. However, the steep angles provide insufficient coverage for thinner, low energy x-ray absorbers. Requiring a thin absorber has made electroplating unsuitable because the typical seed layer is already almost as thick as the completed thin absorber itself. Further, the seed layer causes significant absorber deformation. Also, forming the seed layer and subsequently defining the absorber(s) from the plated wafer generates surface heat. This surface heat can reflow the photoresist distorting the final result and exacerbating the problems.

Thus, there is a need for fabricating relatively large, thin absorbers for sensing low-energy x-rays, below 1 keV, for high resolution spaceborne x-ray spectroscopy applications.

SUMMARY OF THE INVENTION

An aspect of the invention is a large, thin e-beam evaporated absorber with one or more stems electroplated and a relatively shallow angle to the absorber at the stems;

Another aspect of the invention is one or more electroplated stem(s) connected to, and with a relatively shallow angle to, a thin e-beam evaporated absorber that is large enough to sense low-energy electrons at or below 1 keV.

The present invention relates to a method of forming low-energy x-ray absorbers. Sensors may be formed on a semiconductor, e.g., silicon, wafer. A seed metal layer, e.g., gold, is deposited on the wafer and patterned into stem pads for electroplating. Stems, e.g., gold, are electroplated from the stem seed pads through a stem mask. An absorber layer, e.g., gold, is deposited on the wafer, preferably e-beam evaporated. After patterning the absorbers, absorber and stem mask material is removed, e.g., in a solvent bath and critical point drying.

BRIEF DESCRIPTION OF THE DRAWINGS

The foregoing and other objects, aspects and advantages will be better understood from the following detailed description of a preferred embodiment of the invention with reference to the drawings, in which.

DESCRIPTION OF PREFERRED EMBODIMENTS

Figure 1:
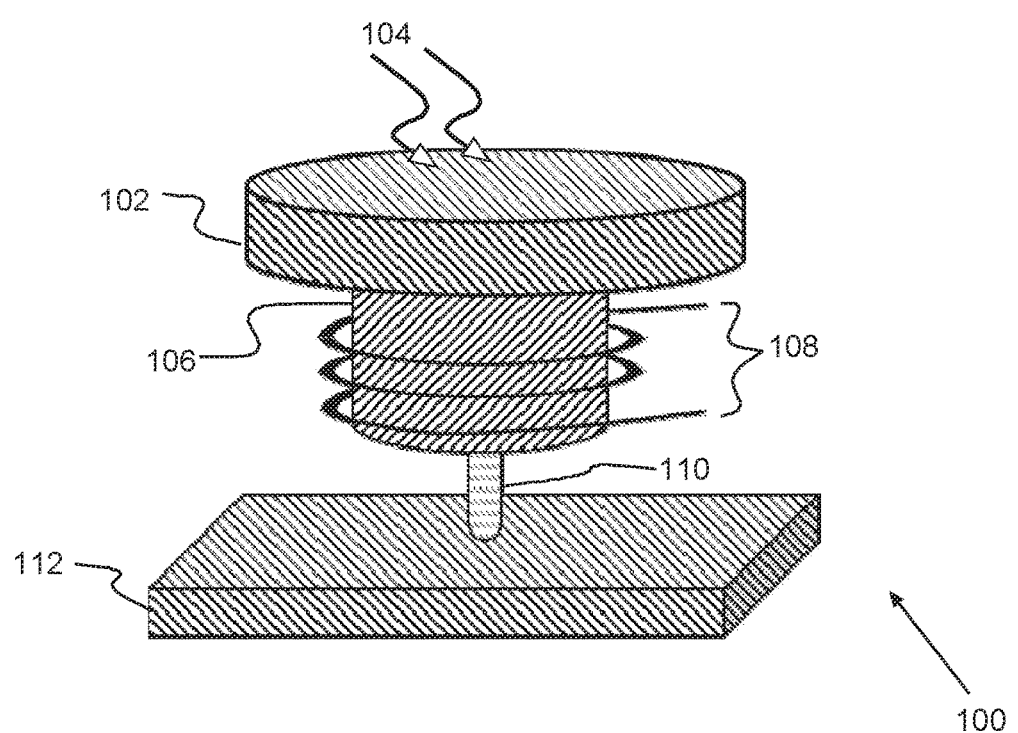
FIG. 1 shows an example of a large low-energy x-ray pixel for use in high-resolution x-ray microcalorimeters with an absorber formed according to a preferred embodiment of the present invention.

Turning now to the drawings and more particularly FIG. 1 shows an example of an ideal large, thin low-energy x-ray pixel 100 for use in high-resolution x-ray microcalorimeters with an absorber 102 formed on a wafer, e.g., a semiconductor wafer, according to a preferred embodiment of the present invention. For sensing low-energy x-rays 104 striking the preferred absorber 102, the preferred absorber 102 is much larger and thinner than prior higher energy x-ray absorbers. An underlying sensor 106 is in intimate contact with, and senses heat generated in, the absorber 102. A stem extending through the sensor 106 to the absorber 102 may pass heat from the absorber 102 to the sensor 106, which couples 108 the sensor 106 response to readout electronics (not shown). The stem of this example also acts as thermal link 110 coupling the sensor 106 to a thermal bath 112, e.g., an underlying semiconductor substrate supporting the pixel 100.

Incoming energy (from low energy x-rays) 104 heats the preferred absorber 102. Heat from the preferred absorber 102 raises the temperature of the underlying sensor 106, primarily through intimate contact between the absorber 102 and sensor 106. Preferably, the sensor 106 is a superconductor requiring operation with a refrigeration system (not shown) capable of cooling the microcalorimeter below 0.1 degrees kelvin (0.1° K). The sensor coupling 108 couples to readout electronics (not shown) e.g., a magnetometer (not shown), such as, a direct current (DC) Superconducting Quantum Interference Device (SQUID) ammeter, for quantifying sensed energy 104. The readout electronics may be formed on the same semiconductor substrate as the pixel(s) 100 using typical integrated circuit processing fabrication techniques. The thermal link 110 couples the sensor 106 to the thermal bath 112. The thermal bath 112 provides a thermal mass that quickly resets the sensor 106 temperature to the bath 112 temperature for a next read.

It is understood that the pixel 100 arrangement of FIG. 1 is for example only and not intended as a limitation. For example, the sensor 106 and thermal link 110 may be at different locations on the absorber 102 so long as the sensor 106 is in intimate contact between the absorber 102. It also should be noted that for optimum mechanical reliability, and to minimize pixel loss during fabrication and cool down (e.g., from collapsing or tearing) the more stems the better for these large thin overhanging absorbers 102. Thus, several of the stems may simply act as thermal links 110 to the thermal bath 112 with the sensor 106 located elsewhere on the absorber.

Previously, large diameter stems (diameter≥30 μm) for higher energy x-ray pixels were defined photolithographically and sputtered on a semiconductor substrate. The stems were about seven (7) times the resist thickness and formed a gentle contact angle (about 40 degrees) between the resist wall and the substrate. Both thermal and athermal phonons, carry energy from the absorber 102 to the thermal bath 112. However, for low-energy pixels 100 these large stems have a large contact area that causes phonon loss degrading microcalorimeter pixel performance. While the energy loss for an individual pixel degrades resolution very little, the positional dependence of the loss of an individual x-ray absorption event worsens energy resolution performance.

However, increasing the number of stems and reducing the stem diameter (≤5 μm) for low-energy pixels 100 to minimize contact area has provided unacceptable results with a steep contact angle near 90 degrees. Thin low-energy x-ray pixels 100 formed according to the present invention have much thinner stems formed with a much gentler angle, and therefore, form reliable low-energy x-ray pixels with collapsing and tearing minimized.

Figure 2:
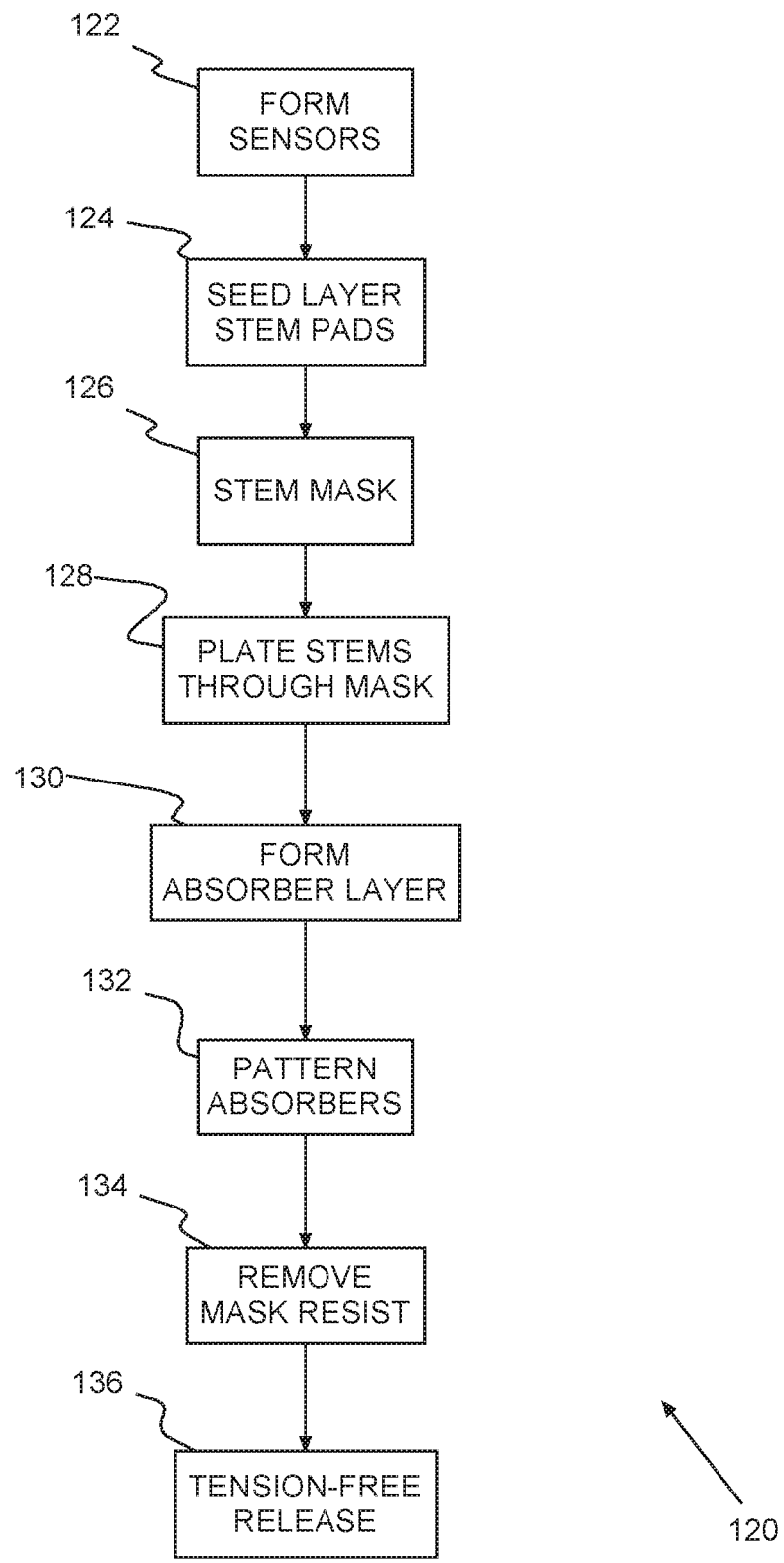
FIG. 2 shows an example of a method of forming preferred absorbers on a semiconductor wafer, according to a preferred embodiment of the present invention.
Figure 3A:
FIGS. 3A-I show formation of preferred absorbers.
Figure 3B:
Figure 3C:
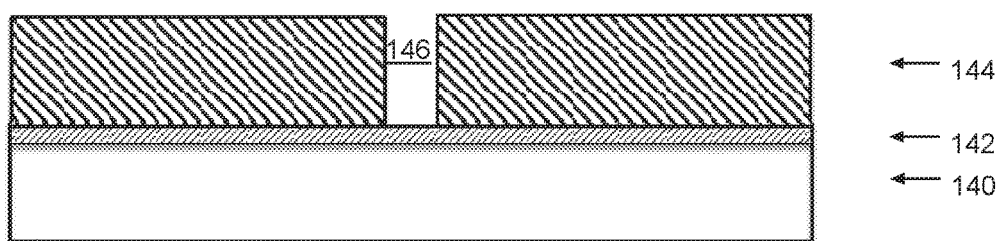
Figure 3D:
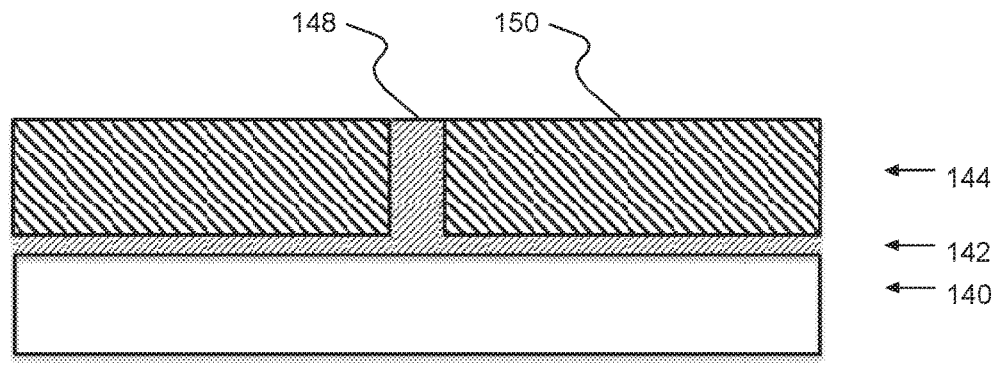
Figure 3E:
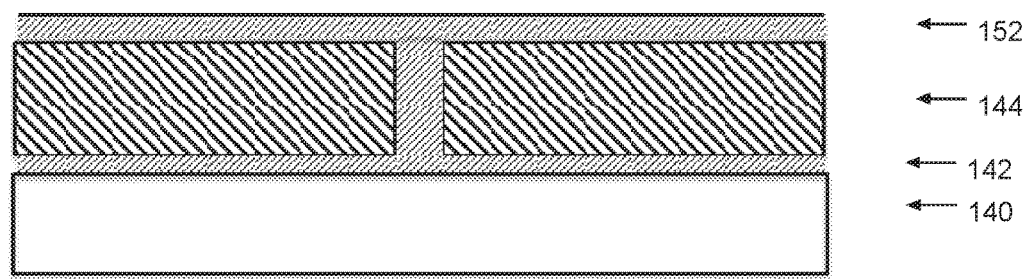
Figure 3F:
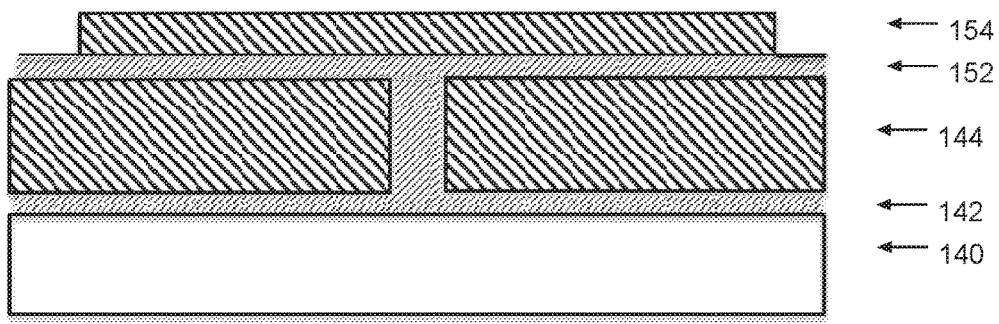
Figure 3G:
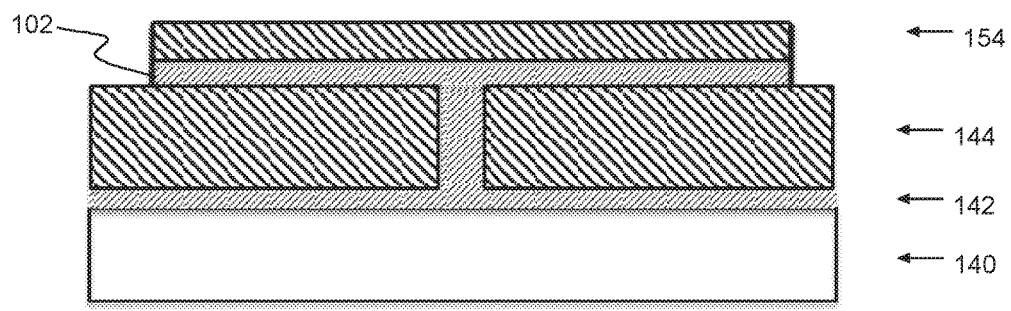
Figure 3H:
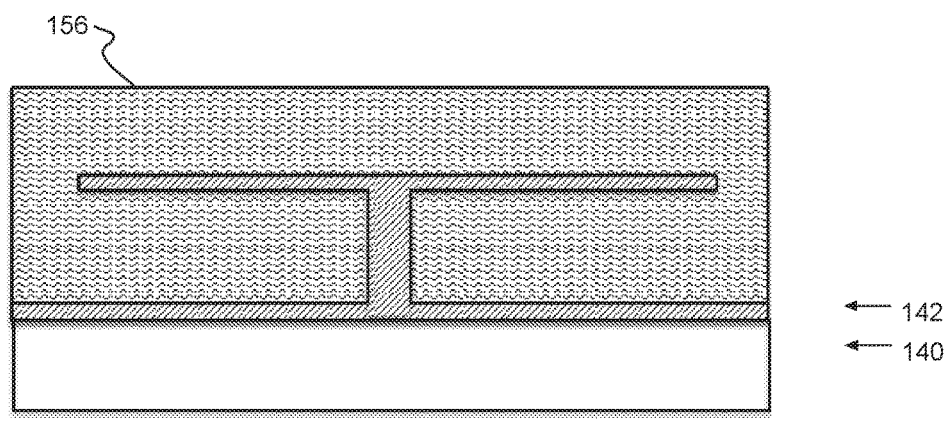
Figure 3I:
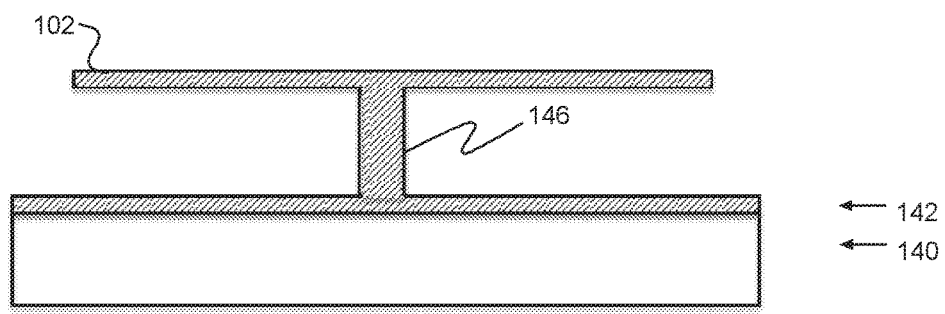

FIG. 2 shows an example of a method 120 of forming absorbers (e.g., 102 FIG. 1) after forming sensors (106 in FIG. 1) on a semiconductor wafer 122, according to a preferred embodiment of the present invention. A seed layer for electroplating is formed 124 on the wafer and patterned, e.g., photolithographically, to define pads for subsequently electroplating stems. A mask layer is formed on the wafer and patterned 126 to define stems above the stem pads. Electroplating from the stem pads through the patterned mask forms 128 stems. A surface absorber layer is formed 130 on the wafer, i.e., stems and stem mask. The absorber layer is patterned 132 to define individual absorbers. The mask material from the stem mask and any absorber pattern mask is removed 134, e.g., in a solvent bath. The solvent is cleared 136 from the wafer.

FIGS. 3A-I show formation of preferred absorbers (e.g., 102 in FIG. 1), which begins forming 122 sensors (106 in FIG. 1) on a clean semiconductor wafer 140, preferably a silicon (Si) wafer. As noted hereinabove, the sensors 106 are fabricated in a selected region on the surface of wafer 140. In this example, the thermal boundary resistance between sensor and substrate materials, together with any thermal resistance between the electron and phonon components of the sensor form the link 110.

Optionally, the wafer 140 may be thinned to a membrane under the selected region(s). In this optional embodiment, the thermal conductance of phonons travelling laterally from the membrane to a subsequently-formed solid support frame portion of the substrate wafer forms the link 110. Also to further improve detector response time, the thermal conductance of the link 110 may be increased for either option by adding a metal film traces (also not shown) from the sensor 106, across the wafer 140 (and/or membrane), to a large metal area of the support frame.

Superconductor niobium traces (not shown) formed on the wafer 140 define pad locations and interconnections. These superconductor traces avoid unwanted thermal links between pixels and/or the frame. The seed layer pads 142 are formed 124 for electroplating stems at the intended stem locations on these superconductor traces. At ultralow superconductor operating temperatures of the microcalorimeter array, the superconducting niobium traces have negligible thermal conductance, unlike normal metals, e.g., titanium (Ti) and gold (Au).

Stem pads 142 are formed 124 by forming an adhesion layer, e.g., a 0.02 μm or less (≤0.02 μm) titanium layer (not shown), on the wafer 140, followed by a thin gold seed layer, 0.2 μm or less (≤0.2 μm). Then, the seed layer and adhesion layer are patterned, e.g., using a suitable mask and etch, to define the stem pads 142 on the wafer 140. Some stem pads 142 are above a sensor 106, and preferably, others are directly on the substrate 140. The stem pads 142 directly on the substrate 140 provide additional support and additional connection to the thermal bath for improved recovery. Preferably also, more than one stem directly connects the absorber 102 to the sensor 106, to provide a strong thermal contact between the absorber 102 and sensor 106.

A stem mask is formed 126 on the stem pads 142, e.g., by depositing a photoresist layer 144 with the mask thickness defining the intended stem length. In particular, the stems are long enough that, wherever the subsequently formed absorbers 102 are not perfectly planar, there is no unintended mechanical contact to the substrate 140. Thus, preferably, the photoresist layer 144 is ≤4.3 μm thick, and preferably, much less than 4.3 μm thick to slow solvent release (132, 134) and minimize any absorber 102 deformation during release. Patterning the mask layer 144 defines stem locations to the stem pads 142, forming an individual mold 146 for each stem. For example, the individual molds 146 may be ≤5.0 μm in diameter, and preferably 53.5 μm with 4.3 μm thick photoresist 144. Preferably, the photoresist is a negative photoresist such that the stem mask pattern prints with an image reversal. The image reversal forms a contact angle at the base of the mold that is greater than 90 degrees (>90°).

Once the mask layer 144 is patterned to define stem molds 146, the wafer is electroplated, e.g., with gold, to form 128 a gold stem 148 in, and filling, each mold 146. Preferably, stem electroplating 128 stops when the upper end of the stems 148 is flush with the upper surface 150 of the mask layer 144.

Absorber heat capacity corresponds to a fixed volume of gold. Spreading that gold volume into as large an absorber area as possible maximizes x-ray photon per pixel collection from a diffuse x-ray source. However, making the absorber ultra-thin, approaching or below the mean x-ray absorption length (0.11 μm) for gold at 1 keV photon energy, does not significantly continue to increase the x-ray photon collection rate. At this ultra-thinness unwanted background effects, "substrate events," also occur more frequently, because x-rays pass through the ultra-thin absorber to be absorbed in the underlying substrate.

Thus, a thin (between 0.35 μm and 0.11 μm thick) absorber layer 152 is formed 130 on the stem mask in contact with the stems 148. Preferably, the absorber layer 152 is a 0.35 μm thick gold layer, electron-beam (e-beam)

evaporated to deposit the absorber layer 152 on the wafer. Prior, thicker absorbers, used for sensing higher energy x-rays, had a higher heat sensing capacity but unacceptably low energy resolution, unacceptable for low x-ray energy, i.e., below 1 keV. A thinner, 0.35 μm gold absorber layer, deposited by e-beam evaporation, is sufficiently thick to absorb 1 keV x-rays, while providing sufficient lateral thermal conductivity for 1 eV energy resolution in one centimeter square (1 cm×1 cm) absorbers 102.

After e-beam depositing the absorber layer 152, fabrication may continue at low temperature, <65° C., below the photoresist melting point and well below the melting point of gold. Low temperature processing maintains the shape of the stem molds 146 and stems 148 undistorted. Also, while the contact angle at the base of the stem is still at or near 90 degrees, maintaining low temperature avoids rounding at the top edges of the stem mold, which can prevent electroplating flush to the top of the mold. Also, rounding the mold top edges, causes electroplated gold to bulge outward in a "pillow" shape. Subsequently, the e-beam evaporated absorber layer self-shadows at these pillow shapes. The self-shadowing causes cracking in the absorber connection around the stems.

After electroplating some upper thickness of the stem mold resist layer may be removed with an oxygen plasma exposure to recess the upper mask surface 150. Removing this upper thickness exposes an upper section of the stem, leaving stubs (not shown) above the mask layer 144. The stubs have a slope that makes favors connection by the e-beam deposition.

Optionally, after plating stems 148 and prior to forming 130 an absorber layer 152, the wafer may be baked at a temperature that spontaneously induces ripples in the upper surface 150 of the mask layer 144. Forming the absorber layer 152 on these optional ripples imparts an undulating surface (not shown) that provides additional strain relief during cooling. Preferably, the absorber layer 152 is an e-beam evaporated gold layer onto the upper surface 150 of the thinned mask 144 and stubs.

The absorber layer 152 is patterned 132 to define individual one centimeter (1 cm) square (1 cm by 1 cm) absorbers 102. For example, the absorber pattern 102 can be defined photolithographically by depositing a low temperature ultraviolet (UV), positive photoresist layer, patterning the photoresist 154 with UV exposure, and a long, low temperature bake to develop the photoresist. Then, removing undeveloped photoresist sets the absorber pattern 154. Etching away exposed gold absorber layer 152 areas in a room temperature wet etch prints the patterned photoresist layer 154 in the absorber layer 152 to define the absorber(s) 102. The defined absorbers 102 cantilever at each stem 148 connection, providing strain relief when the completed microcalorimeter cools to cryogenic operating temperatures.

After defining e-beam evaporated absorbers 102 attached to electroplated stems 148, a suitable solvent bath 156, e.g., acetone followed by methanol, washes away photoresist, removing 134 the stem mask 144 and absorber mask 154 material. Finally a critical point drying removes 136 the solvent in a surface tension-free release. Thereafter, the absorbers 102 are attached to suitable heat sensors, e.g., 106 in FIG. 1, and may be disposed in a microcalorimeter (not shown).

Unlike previously formed, plated absorbers attached to sputtered gold stems, even at low temperature, preferred electroplated gold stem(s) 148 achieve high thermal conductivity with the e-beam evaporated absorber 102. The e-beam evaporated gold absorber 102 stops low-energy (≤1 keV) x-rays, efficiently absorbing x-ray energy. Absorbed energy rapidly thermalizes, conducting heat over the electroplated stem(s) 148, which occupy a small area to minimize parasitic energy loss to the underlying substrate. The high thermal conductivity efficiently transfers heat collected from low energy x-rays to underlying sensors, e.g., 106 in FIG. 1. The resulting microcalorimeter signal has only a negligible dependence upon x-ray absorption position.

Advantageously, preferred e-beam evaporated gold absorbers are relatively large, overhanging thin-film x-ray absorbers that are optimized for soft x-ray spectroscopy. Preferred large absorbers may be 1 cm by 1 cm per pixel, and are thin, e.g., ≤0.3 μm thick, with small gold electroplated stems at a shallow contact angle to the absorber. The electroplated stems, and the e-beam evaporated sensor, form at low temperature, <65° C. to avoid exposing the underlying stem template photoresist to high temperatures, that previously occurred during high temperature mold reflow, bake and ion milling. Thus, preferred low temperature fabrication avoids unintentionally deformed stem template photoresist.

Additionally, the preferred thin-film absorbers are thick enough to stop a sufficient number of incident photons and thermalize quickly, but are still thin enough to keep heat capacity at acceptably low levels. Moreover, the relatively large e-beam evaporated gold absorbers supported by small electroplated gold stems minimize the number of contact points between the temperature sensor and substrate, improving post sensing heat dissipation control.

While the invention has been described in terms of preferred embodiments, those skilled in the art will recognize that the invention can be practiced with modification within the spirit and scope of the appended claims. It is intended that all such variations and modifications fall within the scope of the appended claims. Examples and drawings are, accordingly, to be regarded as illustrative rather than restrictive.

What is claimed is:

1. A method of forming low-energy x-ray absorbers, said method comprising:
    forming stem seed pads on a wafer;
    electroplating stems from said stem seed pads using a temperature below 65° C.;
    deposit an absorber layer above said stems on said wafer using a low temperature; and
    patterning absorbers from said absorber layer;
    wherein said wafer is a semiconductor wafer, and forming said stem seed pads comprises:
    forming superconducting sensors at selected locations on said wafer;
    depositing a seed metal layer onto said semiconductor wafer; and
    patterning said seed metal layer, at least one seed pad being formed at each selected location.

2. A method as in claim 1, wherein the seed metal comprises gold and the semiconductor wafer is a silicon wafer.

3. A method as in claim 2, wherein the gold seed layer is thirty hundredths of a micron (0.35 μm) thick or less (<0.35 μm).

4. A method as in claim 2, wherein the stems and absorber layer are gold and forming superconducting sensors includes forming superconductor traces to one or more stem pad locations.

5. A method as in claim 4, wherein the superconductor traces are formed from niobium.

6. A method as in claim 1, wherein electroplating the stems comprises:
forming a stem mask layer on said stem seed pads;
patterning said stem mask layer to define stems at a temperature below 65° C.; and
electroplating metal through the stem mask pattern from the stem seed pads.

7. A method as in claim 6, wherein the stem seed pads and the stem metal are the same metal and said stem mask layer is thinner than 4.3 µm thick.

8. A method as in claim 7, wherein the stem seed pads include a gold seed layer on a titanium adhesion layer, the stems are gold and patterning said mask layer opens an individual mold <3.5 µm in diameter at each stem location.

9. A method as in claim 1, wherein said upper surface is selectively removed to expose the upper end of each stem, depositing said absorber layer comprises e-beam evaporating absorber material onto the stem mask and exposed stems, and patterning said absorbers is at a temperature below 65° C.

10. A method as in claim 9, wherein patterning said absorbers comprises:
forming an absorber mask layer on said absorber layer;
patterning said absorber mask layer; and
etching exposed areas of said absorber layer.

11. A method as in claim 1, further comprising removing stem and absorber masks, removing said stem and absorber mask comprising:
washing away said absorber mask material and stem mask layer material in a solvent bath; and
removing the solvent.

12. A method as in claim 11, wherein the seed layer, stems and absorber layer are gold, the solvent bath is acetone followed by methanol, and removing the solvent comprises critical point drying said wafer for a surface tension-free release.

13. A method of forming low-energy x-ray absorbers, said method comprising:
forming superconducting sensors at selected locations on a semiconductor wafer;
depositing a seed metal layer onto said semiconductor wafer;
patterning stem seed pads from said seed metal layer, at least one stem seed pad being formed at each selected location;
forming a stem mask on the wafer at a temperature below 65° C.;
electroplating stems through said stem mask from said stem seed pads;
depositing an absorber layer on said stem mask;
forming an absorber mask defining an absorber pattern on said absorber layer;
patterning absorbers from said absorber layer at a temperature below 65° C.;
and removing said absorber mask and said stem mask.

14. A method as in claim 13, wherein the seed metal layer, electroplated stems and absorber layer are gold.

15. A method as in claim 14, wherein depositing said absorber layer comprises e-beam evaporating gold onto said semiconductor wafer and contacting the electroplated gold stems.

16. A method as in claim 15, wherein said semiconductor wafer is a silicon wafer and depositing the gold seed layer comprises depositing a titanium adhesion layer on said silicon wafer and a gold seed layer thirty hundredths of a micron (0.35 µm) thick or less (<0.35 µm) onto said titanium adhesion layer.

17. A method as in claim 15, wherein said stem mask layer is thinner than 4.3 µm thick, said mask layer comprises individual stem molds 3.5-5.0 µm in diameter at each stem pad and electroplating fills each individual mold to the upper surface of said mask layer.

18. A method as in claim 13, wherein removing said absorber mask and stem m ask layer comprises:
washing away mask material in a solvent bath; and
removing the solvent.

19. A method as in claim 18, wherein the solvent bath is acetone followed by methanol, and removing the solvent comprises critical point drying said wafer for a surface tension-free release.

20. A method of forming low-energy x-ray absorbers, said method comprising:
forming superconducting sensors at selected locations on said silicon wafer;
depositing a gold seed layer onto a silicon wafer;
patterning stem seed pads from said gold seed layer, at least one stem seed pad being formed at each selected location;
forming, at a temperature below 65° C., a stem mask thinner than 4.3 µm thick, wherein said stem mask comprises an individual stem mold 3.5-5.0 µm in diameter at each stem seed pad;
electroplating gold stems through said stem mask from said stem seed pads at a temperature below 65° C.;
e-beam evaporating a gold absorber layer on said stem mask;
forming an absorber mask defining an absorber pattern on said absorber layer; patterning absorbers from said absorber layer at a temperature below 65° C.;
washing away absorber mask and stem mask material in a solvent bath; and
removing the solvent.

21. A method as in claim 20, wherein depositing the gold seed layer comprises depositing a titanium adhesion layer on said silicon wafer and a gold layer thinner than 0.35 microns (<0.35 µm) onto said silicon wafer and electroplating fills each individual mold to the upper surface of said mask layer.

22. A method as in claim 20, wherein the solvent bath is acetone followed by methanol, and removing the solvent comprises critical point drying said wafer for a surface tension-free release.

* * * * *